United States Patent
Bienhaus et al.

[11] Patent Number: 5,957,822
[45] Date of Patent: Sep. 28, 1999

[54] LID FOR CLOSING VESSELS

[75] Inventors: Gerhard Bienhaus, Wielenbach; Michael Fritz, Biblis; Jürgen Schwab, Ketsch; Edda Geisler, Mannheim; Herbert Harttig, Altrip; Heinz Macho, Fürth, all of Germany

[73] Assignee: Boehringer Mannheim GmbH, Mannheim, Germany

[21] Appl. No.: 08/617,657

[22] Filed: Apr. 1, 1996

[30] Foreign Application Priority Data

| Apr. 1, 1995 | [DE] | Germany | 295 05 707 U |
| Apr. 1, 1995 | [DE] | Germany | 295 05 652 U |
| Oct. 9, 1995 | [DE] | Germany | 295 16 990 U |

[51] Int. Cl.$^6$ .................................................. B31B 1/74
[52] U.S. Cl. ........................................... 493/100; 29/453
[58] Field of Search ................................ 493/100; 29/453

[56] References Cited

U.S. PATENT DOCUMENTS

| 3,672,122 | 6/1972 | Berger | 493/100 |
| 4,082,200 | 4/1978 | Guest | 29/453 |
| 4,713,219 | 12/1987 | Gerken et al. | 422/102 |
| 4,956,298 | 9/1990 | Diekmann | 430/311 |

FOREIGN PATENT DOCUMENTS

| 705143 | 3/1965 | Canada ................................ 493/100 |
| 1066053 | 1/1954 | France . |
| 1407571 | 9/1964 | France . |
| 1 432 114 | 2/1969 | Germany . |
| 2419501 | 11/1974 | Germany . |
| 85 03 219 | 3/1985 | Germany . |
| 86 22 818 | 8/1989 | Germany . |
| 43 15 726 | 11/1993 | Germany . |
| 42 22 560 | 1/1994 | Germany . |
| 6-8995 | 1/1994 | Japan . |
| 6-278793 | 10/1994 | Japan . |
| 267666 | 11/1947 | Switzerland . |

*Primary Examiner*—Jack W. Lavinder
*Attorney, Agent, or Firm*—Nikaido, Marmelstein, Murray & Oram LLP

[57] ABSTRACT

A lid for closing an opening of a vessel includes a lid body configured to engage the opening, with the vessel having a defined shape. The lid body includes an engagement part which engages a corresponding surface of the vessel, thereby closing the opening. A handling element is disposed on an outer portion of the lid, with the handling element extending in parallel with an axis of the vessel. The handling element is for handling the lid for opening and closing the vessel.

8 Claims, 9 Drawing Sheets

Fig. 2
Fig. 4
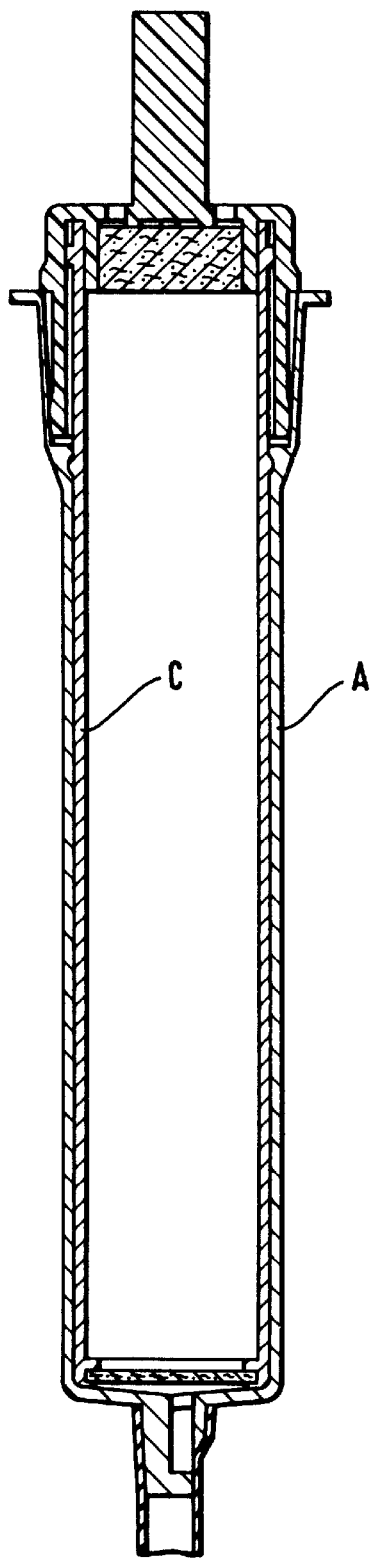
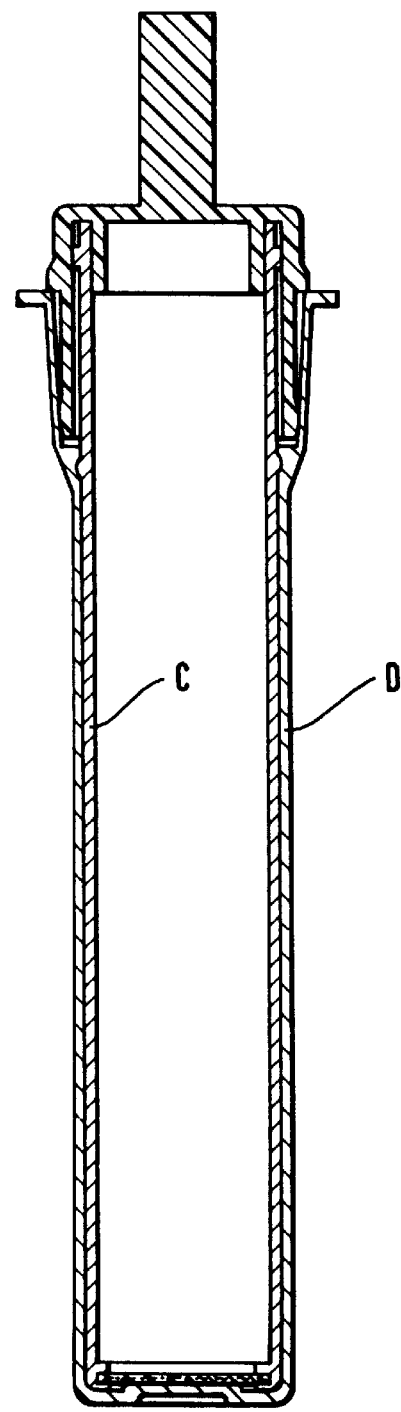

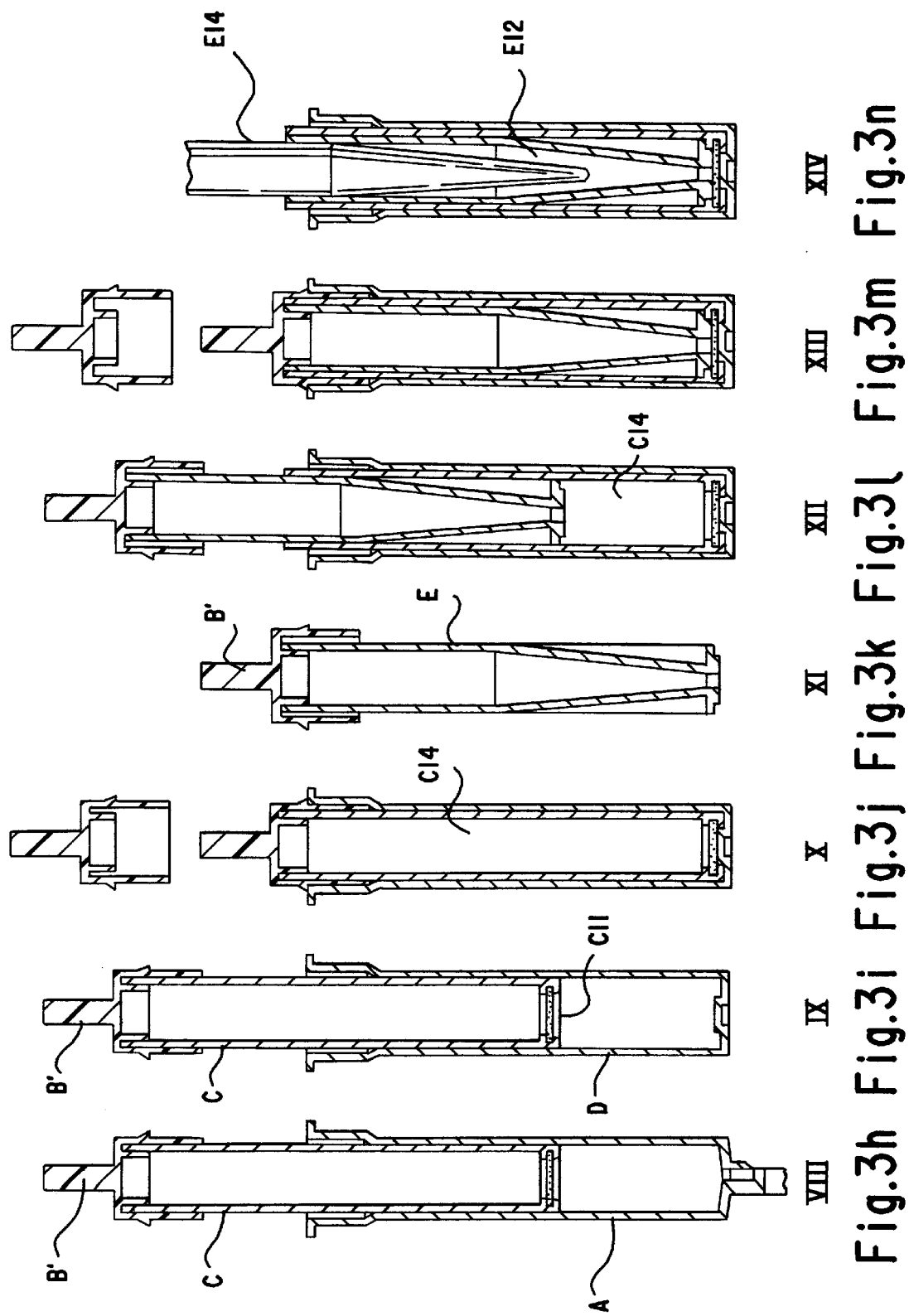

Fig. 5
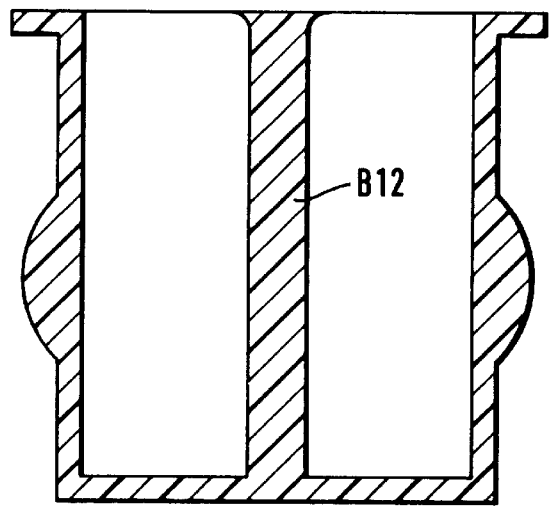
Fig. 6
Position A
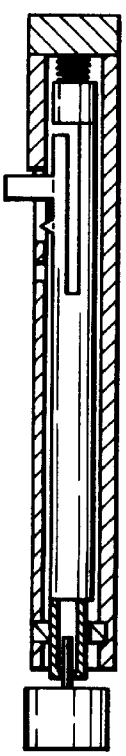
Position B
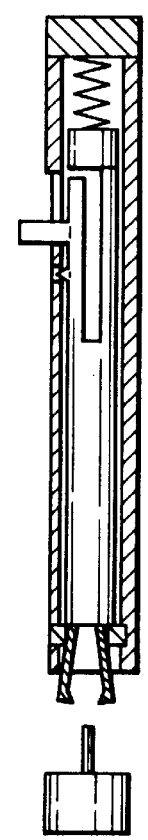

Fig. 7
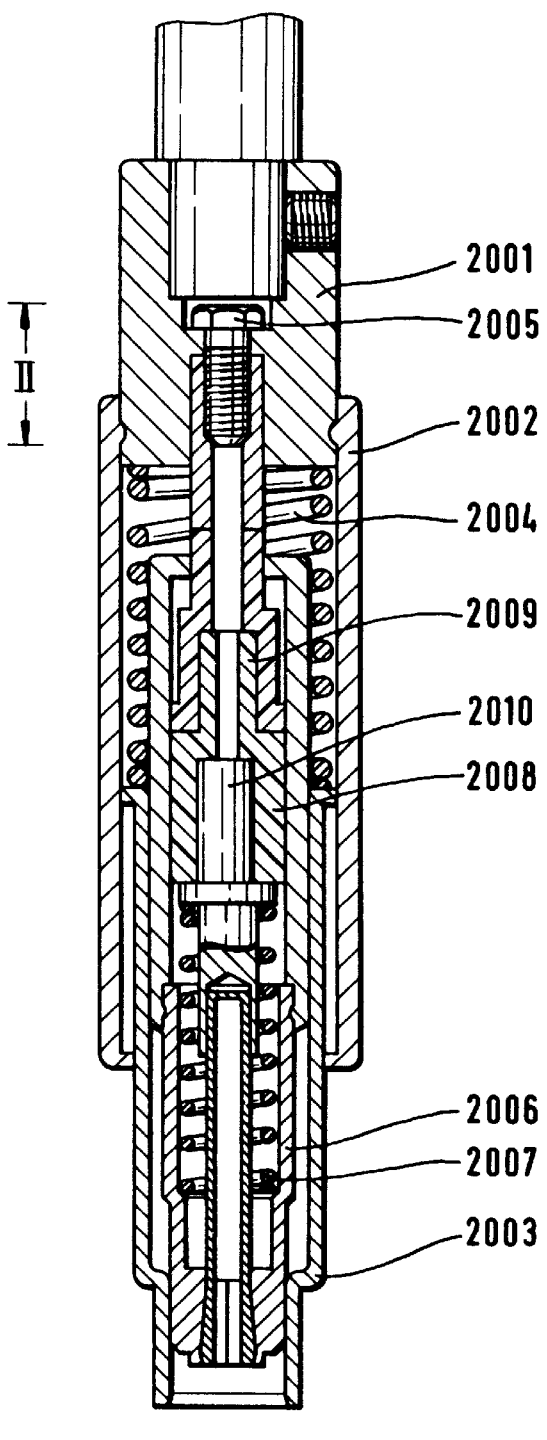
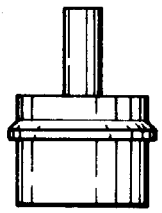

LID FOR CLOSING VESSELS

Subject matters of the invention are a lid for closing the opening of a vessel, a method for closing a vessel using said lid, and a device suitable therefor.

Lids are commonly used to close vessel to reduce influences from the environment which may affect the vessel and/or prevent the escape of liquid from the vessel into the environment. When the vessel is intended to contain a sample whose elements are subject to further treatment or analysis, it is frequently absolutely necessary to have a lid. This applies in particular to the field of analytics related to the health sector, food, environment, and molecular biology. Especially when analyzing particularly low concentrated analytes and analytes bearing a strong resemblance with other analytes, sample contamination which results from the environment has considerable effects on the result of the analysis. This applies in particular to the field of nucleic acid diagnostics. The prevention of contamination and its generation (active prevention) and incorporation of such contamination in the sample (passive prevention) have emerged as a central requirement in nucleic acid diagnostics.

Nucleic acid assays are currently carried out in vessels that either based on the general Eppendorf design (individual vessels) or in the form of microtiter plates (multiple wells). They are generally round and can be closed with a lid. Lids that have been proposed to date are either attached to the sample vessel or to lids of adjacent vessels. This facilitates manual handling of the lids during opening and closing of the vessel. One must also realize that the vessels are very small due to the minute amounts of sample. This applies in particular to formats where numerous reaction vessels are distributed over extremely little space as is the case with the 96 well microtiter plate. Automated use of currently known lids is, hence, impossible or very difficult to implement, i.e. device-operated opening or closing was, hence, difficult, sometimes even impossible.

DE-A-2419510 describes an elastomeric stopper for closing a container. It has, however, the drawback that it can only manually be removed. It has a pressing that requires a considerable amount of force for the lids to be opened. The lid is not suitable for device handling.

DE-A-1432114 describes a stopper having an integrated pipette. The lid has hollow pear-shaped body with highly elastic walls to take up liquid from the bottle into the pipette and eject the liquid again.

DE-U 8622818 describes a bottle for growing and keeping cell cultures which can be closed with a screw cap; the bottle has a filter element whose pore size allow a gas exchange and prevents contamination by microorganisms. A screw cap is used to close the bottle. Moreover, the element does not have an element to handle a structural form which can be introduced into the structural body nor does it have a element that allows the form-fitting grip of a lid with the aid of an device.

U.S. Pat. No. 4,956,298 is a vessel with a lid attached to it. Since lid and vessel are rigidly connected to one another, the lid cannot be used to handle a structural form for introduction into the vessel. Moreover, the lid does not have a element which extends essentially perpendicularly to the closure opening and could serve to move the lid.

U.S. Pat. No. 4,713,219 also describes a vessel with a lid attached to it which is not suitable to handle a structural form for introduction into the vessel. Neither does the lid have a element to move the lid.

FR-1066053 describes a lid which does not allow the introduction of a structural form into the vessel. A form-fitting contact with the lid is not possible.

CH-267666 describes a lid which does not comprise a element for the form-fitting handling of a lid.

DE-G-8503219 describes a closure with a degassing valve comprising a degassing opening with a filter disk. This closure was not designed to handle a structural form for introduction into the vessel. Moreover, it does not comprise an element for the form-fitting handling of the lid.

DE-A4315726 describes a vessel with a lid attached thereto; attached to the lid is a laterally projecting element to manually handle the lid. It is, however, not possible to use this element to introduce a structural form into the vessel.

DE-A 4222560 describes a stopper containing filter material at its upper and lower sides and in its interior. This lid is not suitable for handling a structural form for introduction into the vessels and does not comprise any elements for the form-fitting handling of the lid.

FR-1407571 describes an device for pulling put a stopper. The device has the disadvantage that it is not suited for the exact introduction of the closure as it is necessary that a permanent pressure must be manually exerted on the device to keep it closed.

Subject-matter of the invention is, hence, a lid for closing the opening of a vessel comprising a element that matches the opening of the vessel to be closed and an element which extends essentially perpendicular to the opening for the form-fitting handling of the lid to open and close the vessel using said lid.

It has been found that the handling of lids on a particularly small space can be accomplished in a particularly expedient manner by providing an element which extends essentially perpendicularly to the opening of the vessels. This element odes preferably not extend beyond the lateral outer wall of the vessel. Lids that are used to date have elements which extend horizontally (laterally) beyond the outer wall of the vessels. The lid is preferably a single lid that can be reversibly separated from the vessel.

The type of vessel which can be closed with the lid of the invention is restricted in its use only by the presence of a closable opening (A10). This opening is advantageously located at a well accessible site.

The advantages of the lid of the invention are particularly obvious in vessels that are used in the analysis of sample elements, e.g. body fluids. The vessel to be closed is, hence, preferably, a sample vessel A.

Sample vessels (A) as understood in the invention are vessels which allow storing samples, especially liquid samples or samples bound to a solid matrix; sample vessels are also those wherein original or partially processed samples can be subject to further treatment. They have at least one opening (A10), but may also feature several openings. An additional opening can, for example, be an outlet opening (A11). The outlet opening (A11) can preferably also be closed. Opening (A10) is preferably an opening through which a sample can be introduced into the vessel.

Sample vessels as understood in the invention can have any desired outer shape. Particularly preferred, however, are those with a hollow cylindrical shape, e.g. known from microtiter plates. Preferred sample vessels have an essentially cylindrical shape with an overall length between 100 and 10 mm, particularly preferred appr. 50 mm, an outer diameter between 20 and 5 mm, particularly preferred appr. 9 mm, and an inner diameter which is by 5–1 mm smaller than the outer diameter, particularly preferred appr. 7 mm. Opening (A10) which can be closed through the lid of the invention is preferably located at the one end of the hollow cylinder, particularly preferred at the upper end.

In order to ensure a connection of the vessel as tight as possible, element (B10) is configured such that it tightly embraces from the outside either the part of the vessel which surrounds the opening (e.g. the edge), or, preferably, formfittingly matches the part of the vessel that surrounds the opening (A10) in the interior of the vessel. In order to accomplish this, element (B10) preferably is a circumferential bar the projects into the sample vessel, i.e. a ring beginning at the horizontal part (B17) of the vessel which covers the opening. This bar can be provided with sealing lips (B16) to ensure improved sealing with respect to the sample vessel. The dimensions of the element (B10) are preferably selected such that the lid can be removed from the sample vessel after a given time without destroying the sample vessel or the lid. At the part which projects out of the vessel, the lid preferably has a circumferential edge (overlap B19) which serves as an abutment when inserting the lid into the vessel and also as contamination protection.

Element (B11) is preferably located inside the space surrounded by element (B10). Both element (B10) and element (B11) are preferably configured to match the inner contour (C16) of the structural form such that the structural form remains attached to the element once such an element has been pressed onto an opening of the structural form. Again, this is preferably an annular circumferential bar which, from the inside or outside, formfittingly matches the part of the structural form surrounding the opening. The outer surface of the circumferential is preferably slightly tapered so that the resulting conical shape facilitates handling and retaining of the structural form. The opening of the structural form is also closed using a lid of the invention.

It is a finding of the invention that especially the opening and closing of sample vessels entails a particular risk of contamination. Moreover, it has proven to be disadvantageous to remove the lid during the removal of liquids and gases from the sample vessels. The risk of contamination is particularly high during this time interval. An advantage of a special embodiment of the lid of the invention is that the lid can remain on the vessel even during procedures which entail a gas exchange with the environment, e.g. suction, heating and cooling processes. To accomplish this, the lid, particularly the upper side thereof, is provided with air passage openings (B13). It has proven to be particularly advantageous to cover these air passages with a filter element (b14) in the interior of the lid with respect the interior of the structural form. These filters are preferably made of a plastic, sintered material based on polyethylene, polypropylene or polyether sulfone or polysulfone. Filters of this type are available as sterile filters, for example. The filter serves in particular to prevent aerosols from escaping into the environment; this may be the case during aeration or degassing procedures during sample treatment, e.g. during sample preparation (heating, mixing, and drawing off and when pressing liquid into the interior of the structural form). This simultaneously reduces the carry-over of undesired aerosols/elements from the environment into the sample vessel. The assembly of the filter in the lid is advantageously accomplished such that the cross sections of the air passages take up only a maximum of 10% of the entire effective surface of the filter. The filter material does not rest entirely on the part (B17) of the lid which covers the opening such that a space remains between the surface of the lid where the openings (B13) are and the upper side (effective surface) of the lid. This can be accomplished by means of a spacer (B20) which is attached to the surface. An excessive pressure loss is thus avoided while it is still possible to use the entire surface of the sintered material to allow a medium to pass through.

In a second embodiment, the lid as a structural form grabs and closes a piston (E) which also has an interior (E12). Air passages which are closed by means of aerosol filters are not required as heating/cooling/suction processes are not carried out when such pistons (E) are used. Element (B11) can also close from the outside via opening (E14) of the piston. In a method of isolating nucleic acids from a porous, compressible matrix, piston (E) is designed such that it extends into the a vessel which contains said porous, compressible matrix. In this case, the vessel is referred to as the elution vessel (D). The matrix is preferably a part of the structural form with the piston extending into the interior thereof. By applying pressure on lid (B), the piston is pressed against the matrix, and the liquid which contains the nucleic acid enters into the interior of the piston.

The closure and the handling of the vessels with the aid of the lid of the invention is preferably reversible. If two different vessels are to be closed simultaneously, the frictional connection to each vessel is different. In the aforementioned embodiment, the frictional connection to the structural form (C) is greater than the one to sample vessel (A). In the second embodiment, the frictional connection to the elution vessel (D) and piston (E) is so minor, that the lid is removed from both parts before the piston is removed from the elution vessel.

In a particularly preferred embodiment, the part of the lid which faces away from the sample vessel (outer side) has an element (B12) to grab the lid which extends essentially to the opening. The term "essentially perpendicular" as used in the invention means that element (B12) has a symmetrical axis or plane which is located at an angle between 85 and 90° with respect to a an imaginary plane over the opening. In a particularly preferred manner, the element extends exactly perpendicularly (not considering manufacturing tolerances) from said imaginary plane. When vessel (A) is closed, element (b12) can be located outside the vessel to be closed; it is, however, preferably located inside the vessel to be closed. The element is preferably dynamically balanced, in particular cylindrical with the length of the cylinder being larger than the diameter. It is preferred to have a rather small cylinder diameter. The diameter of the cylinder is smaller than half of the diameter of the part of lid which covers the opening (A10). This ensures a reliable handling of the lid via element (B12) with the aid of a grab in the form of a lid handle. This grab can, for example, be designed as a conventional propelling pencil where tongs are opened when pressure is exerted on a corresponding mechanical element to receive a component, the tongs then close around the cylinder when the pressure is released. Experience has shown that this type of formfitting handling of elements is particularly simple for use with lids to close sample vessels; it can even be implemented on extremely small space as it is the case with 96-well microtiter plate. Reliable functioning (grabbing, positioning), it is particularly expedient if element (B12) has a relatively long guide rail in the pair of tongs. Element (B12) can have grooves (B18) which prevent undesired slipping of the tongs at element (B12) and ensure reliable holding.

A particularly preferred embodiment 1 of lid, a longitudinal section of which is shown in FIG. 1, comprises a cylindrical cap (B) with cylindrical pin (B12) placed thereon and several air passages (B13); the inside of these passages is sealed with an aerosol filter (B14). The annular bars (B11) also serve to attach a filter (B14). Also indicated are the walls of a sample vessel (A) and a structural form (C) having an inner contour (C16) and an outer contour (C12).

FIG. 2 shows a lid when closing a sample vessel (A) and a structural form Ⓒ (embodiment 1).

FIGS. 3a–3n are diagrammatic representations of the intermediate steps of the method of isolating nucleic acids.

FIG. 4 shows a lid in accordance with the invention when closing a structural form (C) and an elution vessel (D) (embodiment 2). A condition when piston (E) is closed and grabbed is shown in FIG. 3m (second-to-last partial figure) and FIG. 8.

FIG. 5 shows a lid where the element (B12) is located above the sample vessel.

FIG. 6 diagrammatically shows an device for handling a lid of the invention. The diagrammatic representation also shows elements for setting the corresponding operating condition (empty, position B, grabbing, position A).

FIG. 7 is a longitudinal section of an improved device for grabbing the lid. Its function is based on the principle of a propelling pencil.

Figure 8:
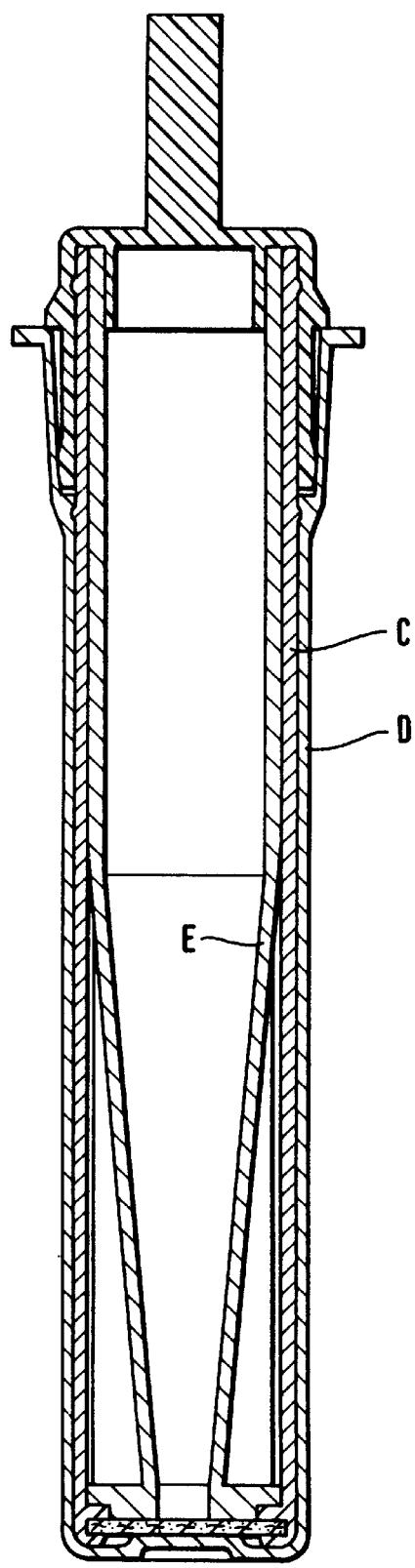

FIG. 8 is a device after assembly comprising a lid, a structural form C, an elution vessel D, and a piston E.

Figure 9:
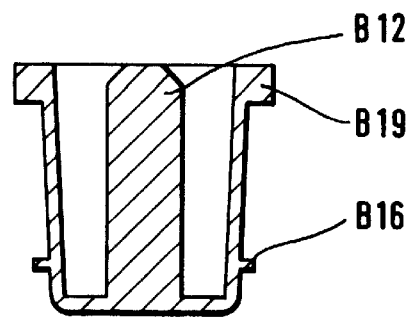

FIG. 9 shows yet another lid where element (B12) is located inside the sample vessel. This vessel also has an overlap and a sealing lip.

Figure 10:
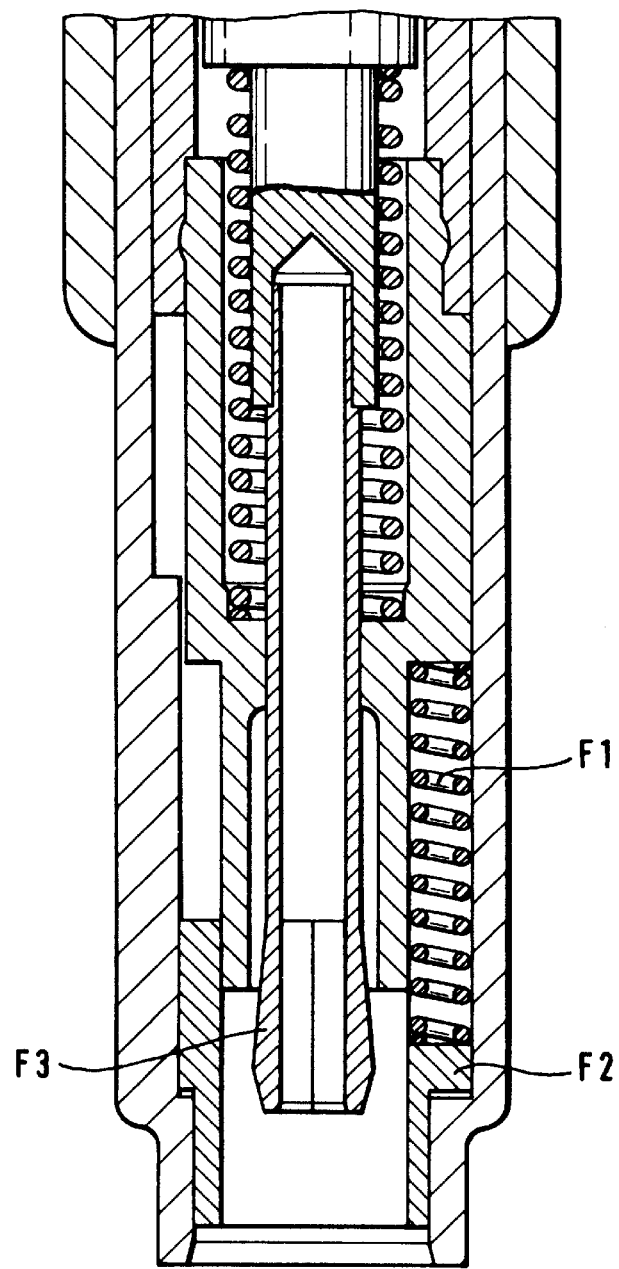

FIG. 10 is the lower part of the device for handling a lid as shown in FIG. 7; however, provision is made for a spring (F1) which, at the side facing toward the lid, has an element that exerts pressure on the lid that is being handled. This can be a ring, for example. When relaxed, element (F2) extends beyond the lower side of the grabbing mechanism (F3). Spring (F1) is set under tension by grabbing the lid and pulling back element (F2) such that the lid is exposed to a permanent pressure which is exerted in direction of the grabbing mechanism; this pressure is not big enough to push the lid, when being grabbed, out of the grabbing mechanism. It is therefore preferred to have a very light spring. In cooperation with component (F2), spring (F1) has the function of pushing the lid out of the grabbing mechanism, once the lid has been released from the mechanism. This is advantageous since the lid does not always move out of the grabbing mechanism when only gravity applies.

Figure 11:
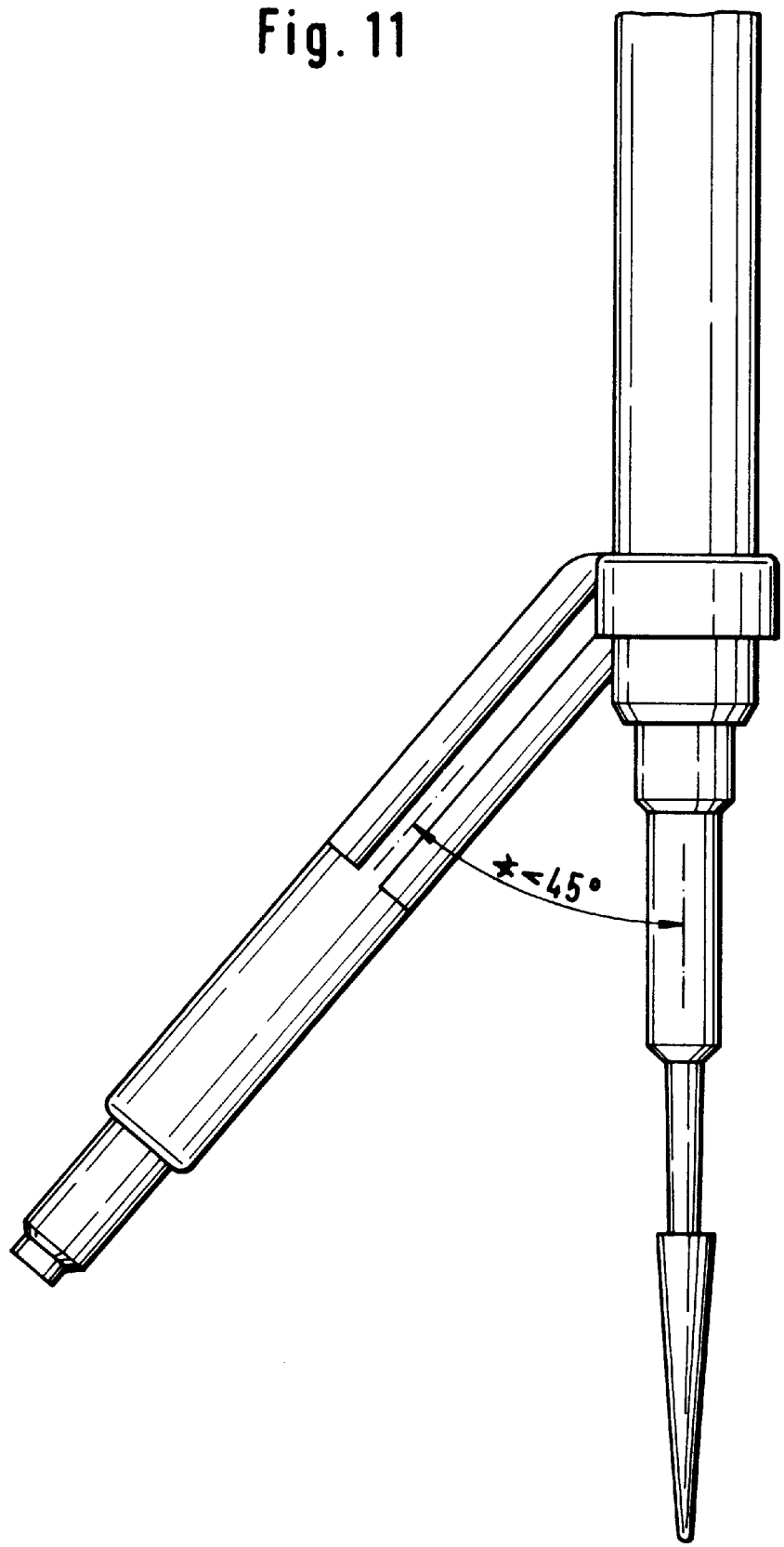

FIG. 11 shows a device for processing lids which comprises an element to clamp element (b12) of the lid and also an element to push lid out of the said element. This device can be advantageously combined with a device for pipetting liquids. A possible device for pipetting liquids can be a commercially available pipette (e.g. by Eppendorf, Germany). It has proven to be particularly advantageous if the longitudinal axes of the two devices form an angle of less than 90°, preferably less than 45°, or as in the example 40°. This device allows reducing the time requirement for operating steps in analytical procedures, i.e. pipetting and opening vessels.

The following are dimensions as they proved to be expedient in accordance with the invention as shown in the first embodiment:

| | |
|---|---|
| outer lid diameter: | 8.8 mm |
| inner lid diameter: | 7.2 mm |
| height of lid including element (B12): | 14.6 mm |
| diameter of air passages (B13) | 0.8 mm |
| height of air passages (B13) | 0.315 mm |
| filter thickness (B14) | 1.6 mm |
| radius of element (B11) | 2.5 mm |
| wall thickness of element (b11) | 0.4 mm |
| height of element (B12) | 7.0 mm |
| diameter of element (B12) | 1.9 mm |

The corresponding inner measures of the sample vessel (a) and the structural form (C) are made to match these measures.

Lids (B) in accordance with the invention can be manufactured in a simple manner by means of injection molding using thermoplastic materials such as polypropylene (Novolen® 110 U.CX). The here mentioned vessels can be manufactured in the same manner. Filter material that may be used can be incorporated at the predetermined sites by means of pressing, gluing and/or sealing. The material of the lid base can under normal conditions not be deformed.

Figures 3A, 3B, 3C, 3D, 3E, 3F, 3G:
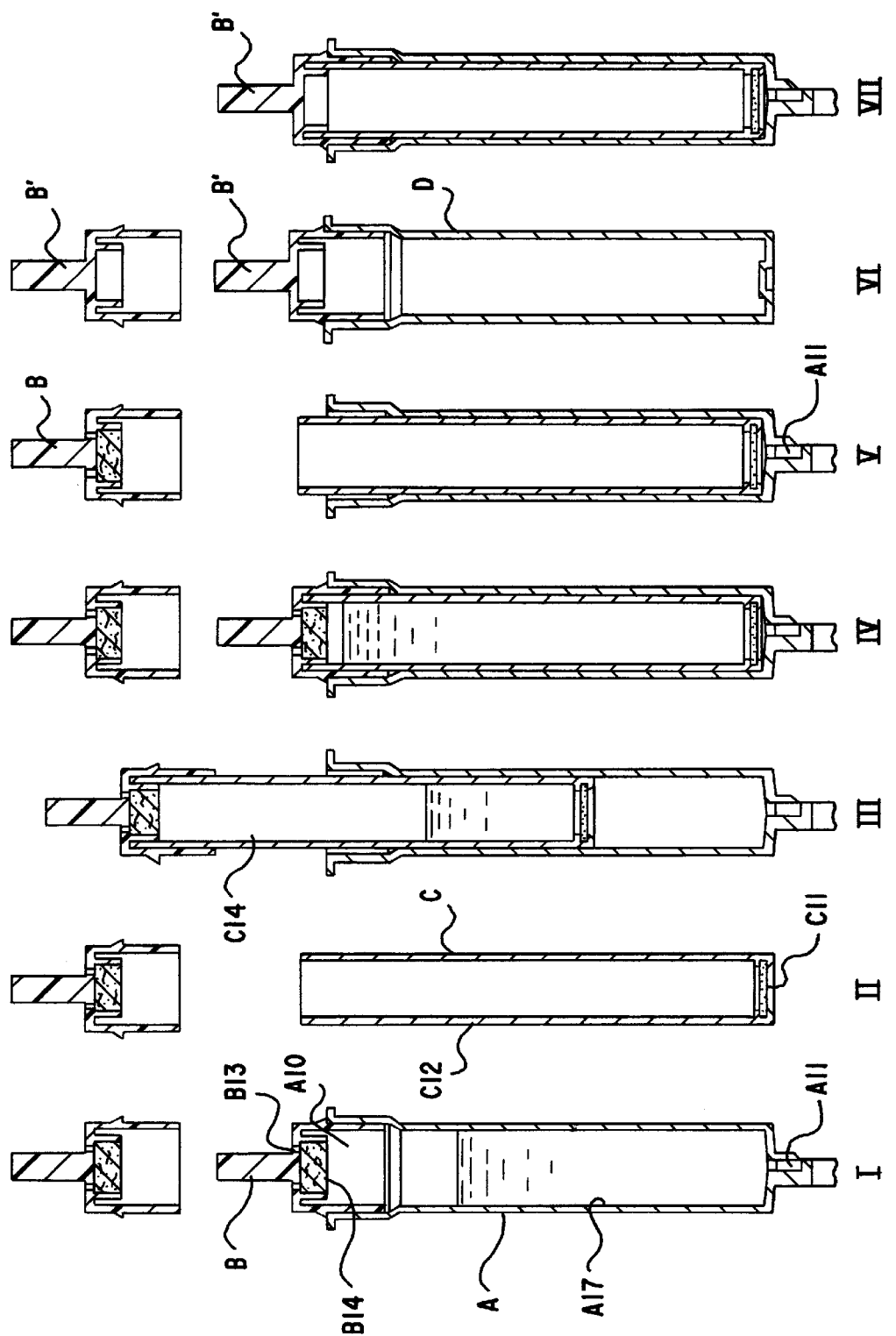

The lid of the invention can preferably be used in methods of isolating nucleic acids. Such a method is in the following described with reference to FIGS. 3a–3n. Lids in accordance with the invention can even be used twice, i.e. to close and handle the sample vessel (A) and the structural form (C) (embodiment 1) as well as the elution vessels (D) and piston (E) (embodiment 2).

In a particular embodiment for processing nucleic acid sample solutions, the following operating steps are carried out. In a first step (I), shown in FIG. 3a, a cell-containing sample liquid is in a sample vessel (A) incubated with a material to which the cells for the separation of nucleic acids are bound. To accomplish this, the material can either exhibit specific binding properties for the surface of the cells, e.g. by immobilizing antibodies against the surface antigens or an absorber material (A16); however, provision can be made for a filter material (A15) to retain the cells when liquid passes through the material, e.g. when removed from the vessel. Conditions for immobilizing cells to surfaces are known to the expert, e.g. Methods in Enzymology, vol. 171, Biomembranes/Part R Transport Theory: Cell and Model Membranes, edited by Sidney Fleischer, Becca Fleischer, Department of Molecular Biology, Vanderbilt University, Nashville, Tenn.

Figure 1:
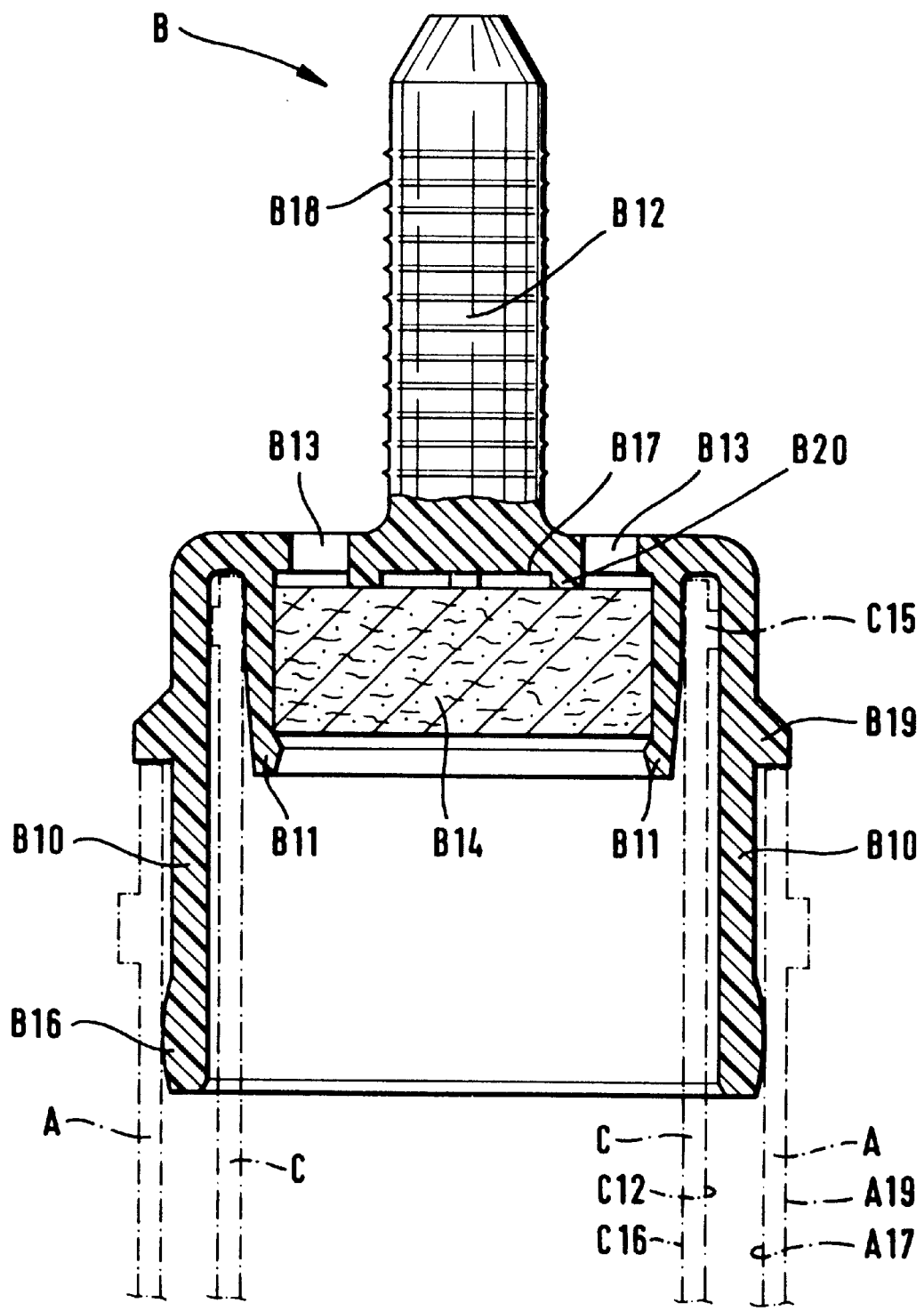

During incubation, the sample vessel is preferably closed with the lid of the invention to ensure active and passive contamination protection. The design of the lid corresponds to the one shown in FIG. 1. It has air passages (B13) which allow air to pass when the lid is placed and pressed in position such that the resulting excess pressure does not press any liquid out of the sample vessel (A) (e.g. via the lower outlet opening).

In another step, the liquid is removed from the sample vessel while cells whose nucleic acids are to be isolated remain in the vessel where they are bound to the material. If the cell-binding material is a particle-type material, the cells can be retained in that the material is magnetic and a magnetic field is applied to the sample vessel from the outside; said field has to be strong enough to retain the particle-type material in the sample vessel when the liquid is removed. The liquid can be removed in different ways. It is, for example, possible to remove the liquid through an outlet opening (A11) which is spatially separated from the inlet opening (A10). If said outlet opening is located in a lower part of the sample vessel and below the retained cells, the liquid can be drawn off, e.g. by applying a minor vacuum. To accomplish this, a valve may be provided at the outlet opening to generate such a low pressure. When drawing off liquid through the valve, the lid (B) can remain on the vessel owing to the presence of the air passages (B13). The air which is drawn into the vessel and passes through is largely freed from contamination due to the filter (B14). bars (B20, FIG. 1) keep the pressure loss to a minimum.

In order to remove other potentially interfering sample components from the cells, it is possible to provide one or several washing steps. To achieve this, washing liquid is filled into the sample vessel; said washing liquid dissolves possible contamination which, however, does not essentially affect the binding of the cells to the surface of the cell-binding material. Such washing solutions are known to the expert, e.g. from cell-separation protocols or corresponding cleaning kit protocols for nucleic acids. They basically depend on how the cells bind to the material.

After the last washing solution has been removed from the sample vessel (A), the purified, enriched cells are brought into contact with a suitable lysis liquid to release the nucleic acids from the cells. The reagents of this lysis solution largely depend on the type of immobilized cells. If the cells are bacteria, the lysis solution preferably contains proteinase K to digest the cell walls. Optionally, the lysis can be supported by heating or cooling and agitating the reaction mixture. If magnetic particles are used as cell-binding material, the mixing can also be accomplished with the aid of a magnet. Moreover, it is possible to mix the solution by shaking the sample vessel. Once digestion is completed, the nucleic acids to be isolated are freely accessible in the solution.

Even during lysis, it is preferred that the reaction vessel be closed by a lid in order to avoid contamination from the environment. After completion of the lysis, the lid is removed, preferably with the aid of a corresponding mechanical device. Subsequently, a structural form (C), whose outer contour (C12) matches the inner contour (A17) of the sample vessel, is introduced into the sample vessel which contains a mixture of digestion products of the cells and the nucleic acids. This structural form is hollow and sealed toward the sample vessel and toward the reaction mixture by means of a filter. The introduction of the structural form (C) is preferably accomplished with the aid of a component (B11) of lid (B) which also contains a component (B10) suitable to close the sample vessel. In this case, the structural form is taken up with the aid of a lid (II) and introduced in the sample vessel while the latter is closed. During this procedure, the reaction mixture can enter the hollow space (C14) of the structural form across filter (C11) (IV). By providing a filter, it is possible to prevent large particles from entering into the hollow space; if the filter already has nucleic acid binding properties, the nucleic acid can already be bound to the filter while the reaction mixture is passing through. In this case, it is expedient to select a glass fiber containing filter material.

In the next step, the remaining lysis reaction mixture is removed from the device consisting of A and C, e.g. by drawing off solution from the sample vessel through an outlet opening (A11) located in the lower portion of the vessel. The solution that has entered the hollow body (C14) of the structural form is, hence, also removed so that the filter more or less no longer contains any liquid. Subsequently, the so far used lid (B) is removed while the structural form (C) still remains in the sample vessel (where it is snapped into position) (V).

Simultaneously or subsequently, an elution vessel (D) is prepared to receive the structural form (C). A lid that can be provided on this vessel, if necessary, is removed (VI). Preferably, an elution solution is provided, e.g. by pipetting, in the elution vessel prior to transferring the structural form (C) into the elution vessel (D). The composition of the elution solution depends on how the nucleic acid is bound to the material in filter (C). It contains reagents which cause the immobilized nucleic acids to elute from the material, i.e. to be released therefrom. Lid (B) initially used to close the elution vessel, is now placed onto the sample vessel (A) with the structural form (C) (VII).

In order to take the structural form (C) out of sample vessel (A), the lid is first removed. The combination of lid and structural form is subsequently introduced into the elution vessel. In a preferred manner, the structural form (C) contains a means (C13K) to fix the structural form in position in the elution vessel (D). Owing to said means, the structural form (C) or the vessel (D) have to be destroyed in order to remove said structural form, or a force has to be applied which exceeds the force necessary to remove the lid (B) from structural form (C). The invention does not propose to remove the structural form from the elution vessel.

While the structural form (C) enters the elution vessel, already provided elution solution enters the matrix (C11) to release the immobilized nucleic acid from the solid matrix. Depending on the amount of prepared elution solution, either only the filter is impregnated with the elution solution or the elution solution enters the hollow body (C14) together with a released nucleic acid. For complete elution of the nucleic acids, the inner contour of the elution vessel should be configured to urge as tightly as possible against the outer contour of the structural form.

In a subsequent step, lid (B) is removed from the combination of structural form (C) and elution vessel (D) (X). Said lid (B) is used to take up a piston (E) (XI) and introduce said piston (E) into the hollow space of the structural form (C) (XII). Said lid engages piston (E) in the inside. The piston is pressed against the filter (C11) such that liquid which is present in the filter passes through an opening located in the contact surface into the interior of the piston. This procedure is particularly effective when the outer contour of the contact surface matches the inner contour of the structural form (C) in at least the area where said pressing is accomplished. Piston (E) can preferably be fixed in this position, e.g. by allowing it to snap into position. Since the so formed device is relatively well sealed by means of the lid, the nucleic acid containing solution can be stored in the device.

In order to remove the desired amount of nucleic acid solution, the lid can be removed (XIII) and the desired amount can be taken out via an opening in the interior of the piston, e.g. by means of pipetting (XIV). Subsequently, the lid can be placed back into position.

The lid of the invention is highly advantageous. It reduces the risk of contaminating samples that are present in the vessel closed by the lid; the lid can also be used in methods employing mechanical devices for opening and closing the vessels. Manual methods using simple hand-operated devices for the opening and closing are, of course also suitable. A very expedient use is the employment as a lid for vessel for the amplification of nucleic acids, e.g. PCR.

Another subject matter of the invention is a method of closing and reopening a vessel (A), characterized in that
a structural form (C) which is handled by a lid (B) is introduced into the vessel such that the lid closes the vessel, and
the lid is removed from the vessel and the structural form (C), while the structural form remains in the vessel.

The structural from preferably has means to snap in a corresponding means of the vessel such that the force necessary to remove the lid is smaller the one necessary to remove the structural form from the vessel.

A particularly preferred method comprised the subsequent removal of the structural form from the vessel with the aid of the lid which grabs the structural form with a force that exceeds the one exerted by the vessel to retain the structural form.

The lid can be processed with the aid of the device of FIG. 7 or FIG. 11 as follows:
The device is placed onto the lid such that element (B12) extends into the clamping mechanism (F3), e.g. as known from ball pens,
when pressure is released, element (B12) is held by clamping mechanism (F3)

The clamping mechanism is released again when pressure is again applied to the device; element (B12) is then released again.

These procedures can preferably be accomplished by allowing the elements to snap into position in the individual operating positions (snap-in positions). In the preferred case, pressure is applied onto the outer surface of the device.

By providing a spring (F1), the lid can be actively released from the clamping device and be securely placed in the sample vessel after a possible shrinkage caused by thermal stress.

The figures also show another advantageous feature of the device for handling lid in accordance with the invention, i.e. the fact that the clamping mechanism exerts a permanent pressure on element (B12) when the lid is being grabbed. This allows exact positioning of the lid on the device to be closed during the closing procedure. The device in accordance with the invention is, hence, particularly well suited for closing a vessel with the aid of a lid and to open vessel that is closed with such a lid.

List of reference numerals

A Sample vessel

10 Inlet opening
11 Outlet opening
15 Filter material
17 Inner form
19 Outer form B Lid 10 Element to close sample vessel A
11 Element to handle structural form G
12 Element to handle lid
13 Air passage
14 Filter element
16 Sealing lip
17 Part of lid which covers opening
18 Grooves
19 Overlap
20 Spacer C Structural form 11 Porous matrix
12 Outer contour
13 Means for fixing the structural form in the elution vessel
14 Hollow body
15 Means for attaching lid
16 Inner contour D Elution vessel E Piston 12 Interior
14 Removal opening F Device for processing lid 1 Spring
2 Element for wiping off liquid
3 Clamping mechanism
2001 housing
2002 sleeve
2003 outer sleeve (movable)
2004 Spring
2005 Ball pen mechanism
2006 clamping sleeve
2007 Spring
2008 Transfer element from 2005
2009 Transter element from 2005
2010 Transfer element from 2005

EXAMPLE

The following is a description with reference to FIG. 7 of how a lid is removed and placed back into position with the aid of a lid handler.

A. Opening the lid

The lid handler must be present with ball pen mechanism in snap-in position A

1. Placing element 2003 (outer sleeve) onto the bar of the tube
2. Exerting a force toward the bottom to lower element (2006) onto the lid while setting spring (2004) under tension. Now, a first pressure point is set.
3. Exerting a force that is greater than the one of step 2.
    a. the clamping mechanism (F3) is pulled over mandrel (B12)
    b. spring (2007) is compressed
    c. the ball pen mechanism (2005) reduces distance II and assumes snap-in position B with spring (2007) remaining under tension.

A second pressure point is set.

4. When the lid handler is released (releasing the pressure exerted toward the bottom), the lid is removed from the tube. The necessary force to overcome friction results from releasing the tension on spring (2004). The force is transferred to the lid and the tube bars via element (2003 and clamping mechanism (F3).
5. The lid handler can now be pulled off and removed together with the lid. The clamping mechanism (F3) is retracted into element (2002) by reducing distance II.

The lid is now partially protected from contamination by element (2203), but extends by 1–2 mm beyond element (2003) in accordance with its function.

B. Closing the lid

6. Placing the lid handler onto the opening of the tube and exerting a force that is directed toward the bottom to push the lid into the opening of the tube.
7. Amplifying the force of item 6. to completely push in the lid and clamping it in position via frictional forces. The force is transferred via elements 2005, 2009, 2008, 2010 and via clamping mechanism (F3).

Spring 2004 is also set under tension

A third pressure point is set.

8. Amplifying the force of item 7. to push the clamping mechanism (F3) out of element (2006). Spring (2004 is further set under tension and ball pen mechanism (2005) reassumes snap-in position A and extends distance II.
9. Reducing the force exerted toward the bottom (release) to push the lid handler completely toward the top while spring (2004) keeps down the tube via element (2003). The spring tension is released during this procedure and the lid handler is ready for further operations.

We claim:

1. A method of opening and closing a vessel, said method comprising the steps of:

providing a vessel having a defined shape and an opening therein;

providing a structural form, said structural form having an outer surface which is configured to fit in the opening of the vessel, said structural form including a lid attached thereto;

inserting the structural form into the opening in the vessel along an axis, whereby the lid engages with and closes the opening in the vessel;

removing the lid from the vessel wherein the structural form remains in the vessel, wherein said step of inserting the structural form into the opening in the vessel includes a step of snapping the structural form into the vessel through engagement of a corresponding engagement means on the structural form and the vessel, whereby a force along the axis which is necessary to remove the lid from the vessel and the structural form is smaller than a force along the axis which is necessary to remove the structural form from the vessel.

2. A method of opening and closing a vessel for preparing reaction mixtures, said method comprising the steps of:

providing a vessel having a defined shape and an opening therein, and containing a reaction mixture;

providing a hollow structural form, said structural form having an outer surface which is configured to match an inner contour of the vessel, said structural form including a lid attached thereto and having a filter sealing an interior of the structural form against the reaction mixture;

inserting the structural form into the opening in the vessel along an axis, whereby the lid engages with and closes the opening in the vessel whereby the reaction mixture enters the interior of the structural form through the filter;

removing the lid from the vessel wherein the structural form remains in the vessel.

3. A method of opening and closing a vessel as recited in claim 2, wherein said step of providing a vessel includes providing the vessel with the defined shape of a hollow cylinder.

4. A method as recited in claim 2, wherein said step of providing the hollow structural form including the lid includes providing the lid with air passages therein.

5. A method as recited in claim 2, wherein said step of providing the structural form with the lid includes providing the filter being disposed therein.

6. A method of opening and closing a vessel, said method comprising the steps of:

providing a vessel having a defined shape and an opening therein;

providing a structural form, said structural form having an outer surface which is configured to fit in the opening of the vessel, said structural form including a lid attached thereto, said lid including air passages therein;

providing a filter element on said lid, said filter element covering the air passages;

inserting the structural form into the opening in the vessel along an axis, wherein the lid engages with and closes the opening in the vessel;

removing the lid from the vessel wherein the structural form remains in the vessel.

7. A method as recited in claim 6, wherein said steps of providing the lid and providing the filter element includes a step of providing spacer elements on the lid adjacent the air passages, wherein the spacer elements maintain a space between the filter element and an inner surface of the lid.

8. A method as recited in claim 7, wherein said step of inserting the structural form into the opening in the vessel includes a step of snapping the structural form into the vessel through engagement of a corresponding engagement means on the structural form and the vessel, whereby a force along the axis which is necessary to remove the lid from the vessel and the structural form is smaller than a force along the axis which is necessary to remove the structural form from the vessel.

* * * * *